United States Patent
Nishiie et al.

(10) Patent No.: US 7,871,372 B2
(45) Date of Patent: Jan. 18, 2011

(54) ENDOSCOPE, ENDOSCOPE SYSTEM, AND FILTER UNIT

(75) Inventors: Takehiro Nishiie, Tokyo (JP); Atsushi Watanabe, Tokyo (JP); Hiroki Moriyama, Tokyo (JP)

(73) Assignee: Olympus Corporation, Tokyo (JP)

( * ) Notice: Subject to any disclaimer, the term of this patent is extended or adjusted under 35 U.S.C. 154(b) by 1207 days.

(21) Appl. No.: 11/490,000

(22) Filed: Jul. 20, 2006

(65) Prior Publication Data

US 2006/0293564 A1 Dec. 28, 2006

Related U.S. Application Data

(63) Continuation of application No. PCT/JP2005/000772, filed on Jan. 21, 2005.

(30) Foreign Application Priority Data

Jan. 21, 2004 (JP) ............................. 2004-013522

(51) Int. Cl.
*A61B 1/00* (2006.01)
(52) U.S. Cl. ..................... 600/154; 600/101; 600/133; 600/153; 600/159
(58) Field of Classification Search ......... 600/101–102, 600/158–159, 153, 133
See application file for complete search history.

(56) References Cited

U.S. PATENT DOCUMENTS

| 4,878,484 | A | * | 11/1989 | Miyagi | 600/133 |
| 5,343,854 | A | * | 9/1994 | Katsurada | 600/146 |
| 5,547,456 | A | * | 8/1996 | Strobl et al. | 600/133 |
| 5,580,530 | A | * | 12/1996 | Kowatsch et al. | 422/102 |
| 5,723,090 | A | * | 3/1998 | Beerstecher et al. | 422/26 |
| 5,868,667 | A | * | 2/1999 | Lin et al. | 600/133 |
| 5,871,441 | A | * | 2/1999 | Ishiguro et al. | 600/133 |
| 5,876,331 | A | * | 3/1999 | Wu et al. | 600/139 |
| 6,641,781 | B2 | * | 11/2003 | Walta | 422/28 |
| 6,679,835 | B2 | * | 1/2004 | Moriyama | 600/133 |
| 2004/0041031 | A1 | * | 3/2004 | Root et al. | 235/487 |

FOREIGN PATENT DOCUMENTS

| JP | 2000-51323 | 2/2000 |
| JP | 2000-102508 | 4/2000 |
| JP | 2004-73259 A | 3/2004 |
| WO | WO 03/079888 A2 | 10/2003 |

OTHER PUBLICATIONS

Supplementary European Search Report dated Aug. 26, 2009.

* cited by examiner

*Primary Examiner*—Matthew J Kasztejna
(74) *Attorney, Agent, or Firm*—Scully, Scott, Murphy & Presser, P.C.

(57) ABSTRACT

An endoscope includes an insertion portion; a channel member that has one opening at a distal portion of the insertion portion and other opening at a portion other than the distal portion; an exterior member opening that communicatively connects an interior of the endoscope to outside; and a filter that is provided at the exterior member opening to prevent at least one of intrusion of dust into the interior and leakage of a lubricant agent stored in the endoscope out of the endoscope.

11 Claims, 6 Drawing Sheets

ENDOSCOPE, ENDOSCOPE SYSTEM, AND FILTER UNIT

CROSS-REFERENCE TO RELATED APPLICATIONS

This application is a continuation of PCT international application Ser. No. PCT/JP2005/000772 filed Jan. 21, 2005 which designates the United States, incorporated herein by reference, and which claims the benefit of priority from Japanese Patent Application No. 2004-013522, filed Jan. 21, 2004, incorporated herein by reference.

BACKGROUND OF THE INVENTION

1. Field of the Invention

The present invention relates to an endoscope, an endoscope system, and a filter unit, and more particularly to an endoscope, an endoscope system that has a high temperature and high pressure steam supplying device for sterilizing the endoscope by a high temperature and high pressure steam, and a filter unit that is used for the endoscope.

2. Description of the Related Art

Conventionally, an endoscope is widely used in a medical field and the like. An operator can observe an internal organ in a body cavity by inserting an elongated insertion portion of the endoscope into the body cavity, and perform various types of medical treatments using medical instruments inserted through a medical instrument insertion channel when necessary.

A bendable portion and a distal portion are provided at a distal end of the insertion portion, and the operator and the like can change an observation direction of an objective lens of an observation optical system disposed in the distal portion by bending the bendable portion and the distal portion through a wire connected to a manipulator unit of the endoscope.

In order to prevent infections from spreading among patients, an exterior surface of the endoscope and an interior of a channel member such as the insertion channel disposed in an interior covered by an exterior member of the endoscope must be disinfected and sterilized after completion of patient inspection and the like using the endoscope. Conventionally, the disinfection and the sterilization are performed by using an antiseptic solution and a gas such as an ethylene oxide gas (EOG).

However, when the sterilizing gas is used for the disinfection and the sterilization of the endoscope, management of the endoscope after the disinfection and the sterilization is troublesome. For example, aeration is necessary in order to sufficiently remove a sterilizing gas adhered on the endoscope after the disinfection and the sterilization. Further, there is a problem that a high running cost is required to use the sterilizing gas.

Management of the antiseptic solution is also complicated for the operator when the antiseptic solution is used for the disinfection and the sterilization of the endoscope. Further, a high cost is required to dispose the used antiseptic solution.

To cope with the above problems, recently, a method and a device for a high temperature and high pressure steam sterilizing process (referred to as autoclave process in the following) which have a low running cost and do not require the troublesome operation, come to be widely used as the method and the device for the sterilization of the endoscope device.

A method of the autoclave process for preventing damage of an outer coat of the endoscope due to a difference in pressure between the inside and outside of the endoscope is proposed (for example, see Japanese Patent Application Laid-Open No. 2000-51323). According to the method, in order to prevent the damage, an inlet (hereinafter, referred to as a steam inlet) through which the high temperature and high pressure steam is supplied into the interior covered by the exterior member of the endoscope is provided in the exterior member of the endoscope; the steam enters the endoscope interior when the autoclave process is performed.

SUMMARY OF THE INVENTION

An endoscope according to one aspect of the present invention includes an insertion portion; a channel member that has one opening at a distal portion of the insertion portion and other opening at a portion other than the distal portion; an exterior member opening that communicatively connects an interior of the endoscope to outside; and a filter that is provided at the exterior member opening to prevent at least one of intrusion of dust into the interior and leakage of a lubricant agent of the interior of the endoscope out of the endoscope.

An endoscope system according to another aspect of the present invention includes the endoscope according to the present invention; and a high temperature and high pressure steam supplying unit that supplies high temperature and high pressure steam into the interior of the endoscope and into the channel member from the outside of the endoscope.

A filter unit according to still another aspect of the present invention is for an endoscope including a channel member therein which has a plurality of openings at an exterior space and an exterior member provided with an exterior member opening for supplying high temperature and high pressure steam for sterilization into an interior of the endoscope while performing a sterilizing process. The filter unit includes a filter that is arranged near the exterior member opening while at least performing the sterilizing process for preventing at least one of intrusion of dust into the interior and leakage of a lubricant agent stored in the endoscope out of the endoscope.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention will be described below with reference to the accompanying drawings.

Figure 1:
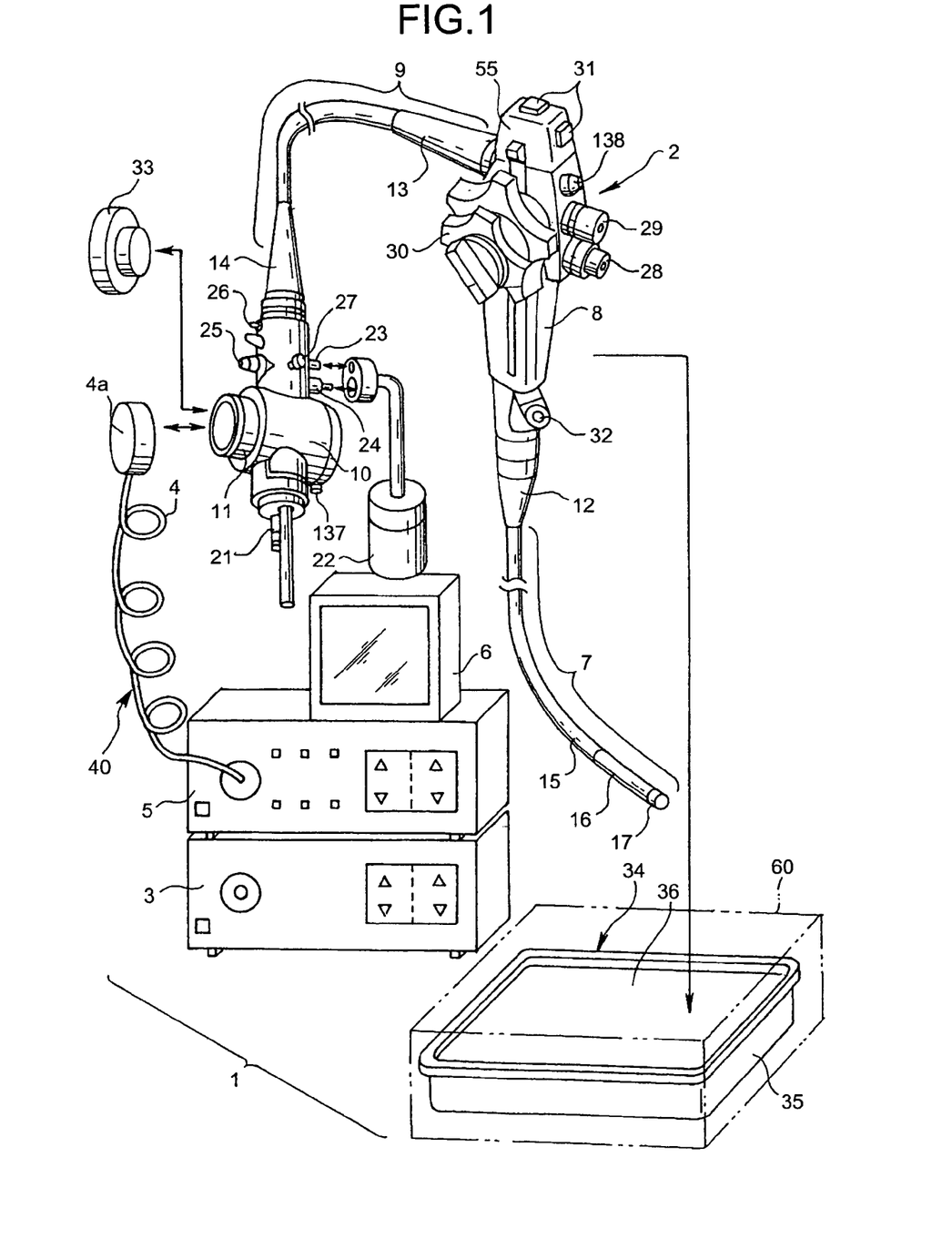
FIG. 1 is a perspective view schematically showing a configuration of an endoscope and an endoscope system according to a first embodiment of the present invention.
Figure 2:
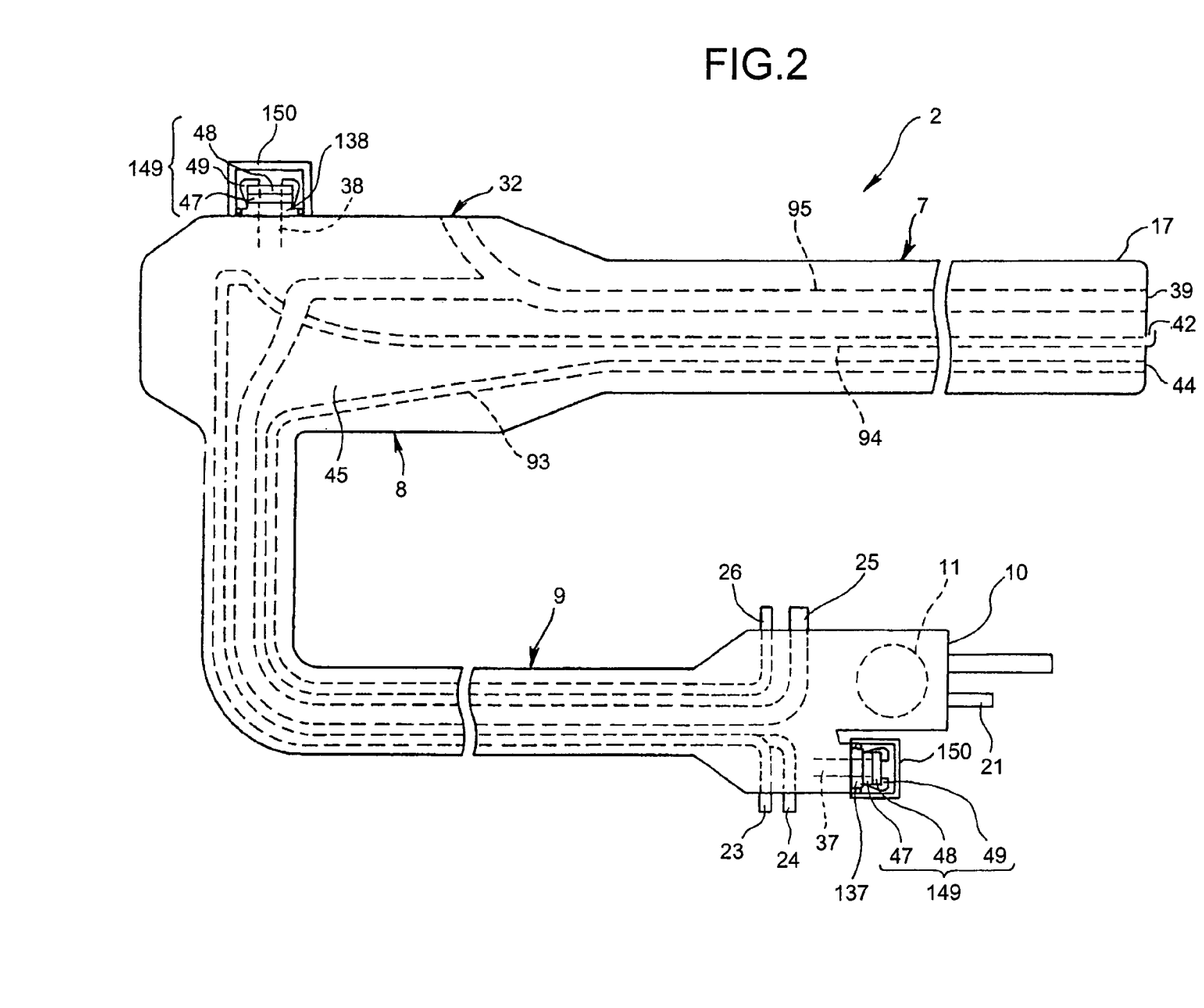
FIG. 2 is a perspective front view schematically showing the interior of the endoscope in FIG. 1.

FIG. 1 is a perspective view schematically showing a configuration of an endoscope and an endoscope system according to a first embodiment of the present invention, and FIG. 2 is a perspective front view schematically showing the interior of the endoscope in FIG. 1.

As shown in FIG. 1, an endoscope system 1 includes an endoscope device 40 that has an endoscope 2, and a high temperature and high pressure steam supplying device (hereinafter, referred to as a supplying device) 60 as being a high temperature and high pressure steam supplying unit that houses a sterilizing case (hereinafter, referred to as a case) 34, and the case 34 houses a part of the endoscope device 40 when an autoclave process is performed.

The endoscope device 40 has basic components including the endoscope 2 that has an imaging unit such as a solid-state image sensor and an imaging lens not shown, a light source device 3 that is detachable with respect to the endoscope 2 and supplies an illuminating light to an optical guide not shown provided in the endoscope 2, a video processor 5 that controls an operation of the imaging unit of the endoscope 2 as well as processes an image signal acquired from the imaging unit while the video processor 5 is connected to the endoscope 2 through a signal cable 4, and a monitor 6 that displays the image signal corresponding to a subject image output from the video processor 5.

The endoscope 2 includes members that have resistance to high temperature and high pressure steam so that the autoclave process can be performed after the endoscope 2 is used for observation, treatment, and the like, and a so-called bedside rinsing is performed on the endoscope 2.

The endoscope 2 has basic components including a elongated flexible insertion portion 7, a manipulator portion 8 that is connected to a proximal end side of the insertion portion 7, a flexible universal cord 9 whose one end is connected to a first face of the manipulator portion 8, a connector portion 10 that is provided at the other end of the universal cord 9 and detachably attached to the light source device 3, and an electronic connector portion 11 that is provided on an exterior periphery face of the connector portion 10. Here, a connector 4a of the signal cable 4 detachable with respect to the video processor 5 is detachably attached to the electronic connector portion 11.

An insertion portion side bending preventing member 12 that consists of elastic material for preventing a connection connecting the insertion portion 7 and the manipulator portion 8 from being bent sharply. Further, a manipulator portion side bending preventing member 13 is provided at a connection portion connecting the manipulator portion 8 and the universal cord 9, and a connector portion side bending preventing member 14 is provided at a connection portion connecting the universal cord 9 and the connector portion 10.

The insertion portion 7 has basic components including a flexible channel portion 15, a bendable portion 16 that is provided at a distal end side of the flexible channel portion 15 and bent by a rotation of a bending manipulator knob 30 of the manipulator portion 8, and a distal portion 17 that is provided with a system such as an observational optical system and an illumination optical system not shown and provided at a distal end, which is one end of the insertion portion 7.

Further, a liquid channel 93 as being a channel member having one end connected to a liquid supplying opening 44 described later that is one opening provided at the distal portion 17 and the other end connected to an injection venting cap 26 that is the other opening provided at the connector portion 10; an air/water channel 94 as being a channel member having one end connected to an air/water nozzle 42 described later that is one opening provided at the distal portion 17 and the other ends connected to a water tank pressurizing venting cap 23 and a liquid supplying venting cap 24 that are the other openings provided at the connector portion 10; and an aspiration channel 95 as being a channel member having one end connected to an aspiration opening 39 described later that is one opening provided at the distal portion 17 and the other ends connected respectively to a medical instrument insertion opening 32 that is other opening and an aspiration venting cap 25 that is other opening provided at the connector portion 10, are provided in an interior (hereinafter, referred to as an interior) 45 whose regions except for an exterior member opening described later and the other opening of the insertion portion 7 and the universal cord 9 are covered by an exterior member (see FIG. 2).

As described above, the endoscope 2 houses various channels inside into which a fluid and the like can be inserted and whose ends open to the outside. The insertion portion 7 and the universal cord 9 are both formed from a flexible material, and formed in a hollow not solid. Further, most of the channels 93, 94, and 95 inside the insertion portion 7 and the universal cord 9 are provided in the hollow without being secured therein, and there are many spaces among the channels and few other built-in components.

A periphery of each of the channels 93, 94, and 95 at middle portions thereof (this refers to a position away from the end portions thereof, and refers to a substantially wide region) is communicatively connected to the endoscope interior 45, and the endoscope interior 45 is communicatively connected to the outside by exterior member openings 37 and 38 described later. In other words, the channel periphery is communicatively connected to the outside through the endoscope interior 45 and the exterior member openings 37 and 38. The channel periphery can be selectively brought into/out of the communicatively connected state by attachment/detachment of a watertight cap 150.

In the present embodiment, a space where the endoscope interior 45 is formed is provided, for example, around a portion of the channel at a middle of a channel route that connects the two openings without filling the endoscope interior 45 of the endoscope 2 by a filling agent or a solid body. Further, various built-in components and parts are provided at a middle of a route between the endoscope interior 45 and the exterior member openings 37 and 38; however, the built-in components and the parts are arranged in a way not to block the steam. Therefore, the steam can be supplied through the route without any disturbance.

The distal portion 17 is provided with the air/water nozzle 42 connected to the one end of the air/water channel 94, the aspiration opening 39 that is an opening at the distal end side of a medical instrument channel connected to the one end of the aspiration channel 95, and a liquid supplying opening 44 connected to the one end of the liquid channel 93. The air/water channel 94 is used when liquid and air used for rinsing are injected towards an optical member on an exterior surface of the observational optical system not shown by pressing an air/water supplying manipulator button 28 described later of the manipulator portion 8. The aspiration channel 95 is for inserting the medical instrument into the insertion portion 7 and for aspirating liquid inside the body cavity. The liquid channel 93 is for injecting liquid towards an observational object.

An end portion of the connector portion 10 is provided with an air venting cap 21 that is detachable with respect to an air source, not shown, built inside the light source device 3. Further, the water tank pressurizing venting cap 23 and the liquid venting cap 24 that are detachable with respect to a water tank 22 are provided at a position on an exterior periphery face of the connector portion 10 and at a position other than a position at which the electronic connector portion 11 is provided. Here, the water tank 22 is a liquid source.

The other end of the air/water channel 94 is connected to the water tank pressurizing venting cap 23 and the liquid venting cap 24. The water tank pressurizing venting cap 23 and the liquid venting cap 24 have openings for supplying the high temperature and high pressure steam into the air/water channel 94 disposed in the endoscope interior 45 of the endoscope 2 when the autoclave process is performed. In other words, the water tank pressurizing venting cap 23 and the liquid venting cap 24 are the steam inlet that supplies the steam into the air/water channel 94 in order to sterilize the air/water channel 94 interior.

Further, the aspiration venting cap 25, which is connected to an aspiration source not shown for performing aspiration by the aspiration opening, is provided at the exterior periphery face of the connector portion 10 and at a position substantially opposite to a position of the water tank pressurizing venting cap 23 and the liquid supplying venting cap 24. The other end of the aspiration channel 95 is connected to the aspiration venting cap 25. The aspiration venting cap 25 has an opening for supplying the high temperature and high pressure steam to the aspiration channel 95 disposed in the endoscope interior 45 of the endoscope 2 when the autoclave process is performed. In other words, the aspiration venting cap 25 is the steam inlet for supplying the steam into the aspiration channel 95 in order to sterilize the aspiration channel 95 interior.

Further, the injection venting cap 26, which is connected to a water supplying unit not shown for supplying water from the liquid supplying opening, is provided on the exterior periphery face of the connector portion 10 near the aspiration venting cap 25. The other end of the liquid channel 93 is connected to the injection venting cap 26. The injection venting cap 26 has a venting cap that is an opening for supplying the high temperature and high pressure steam to the liquid channel 93 disposed in the endoscope interior 45 of the endoscope 2 when the autoclave process is performed. In other words, the injection venting cap 26 is the steam inlet for supplying the steam into the liquid channel 93 in order to sterilize the liquid channel 93 interior.

Further, a grounding terminal venting cap 27 is provided on the exterior periphery face of the connector portion 10 and near the aspiration venting cap 25, water tank pressurizing venting cap 23, and the liquid venting cap 24. The grounding terminal venting cap 27 is used to return leaked current back to a high frequency medical treatment device when high frequency current leakage is occurred at the endoscope due to performing a high frequency medical treatment and the like.

A watertight cap 33 is detachably attached to the electronic connector portion 11 of the connector portion 10. Further, the watertight cap 33 is attached after the connector 4a of the signal cable 4 is detached in order to prevent entry of a rinsing solution into the connector portion 10 while rinsing or to prevent entry of the high temperature and high pressure steam into the endoscope interior 45 of the endoscope 2, while performing the autoclave process. Further, a pressure adjusting check valve not shown is provided on the watertight cap 33.

A venting cap 137 that has the exterior member opening 37 is disposed near a face at which the electronic connector portion 11 of the connector portion 10 is disposed. The venting cap 137 having the exterior member opening 37 is for supplying the high temperature and high pressure steam into the endoscope interior 45 of the endoscope 2 when the autoclave process is performed. In other words, the venting cap 137 is the steam inlet for supplying the steam into the endoscope interior 45.

The interior of the liquid channel 93, the interior of the air/water channel 94, and the interior of the aspiration channel 95 are heated from outside thereof by supplying the high temperature and high pressure steam into the endoscope interior 45 when each of the channel interiors is sterilized by the autoclave process in which the high temperature and high pressure steam is supplied into the liquid channel 93, the air/water channel 94, and the aspiration channel 95. Consequently, a sterilizing temperature is uniformly maintained for an entire region of each of the channels, and each of the channel interiors is certainly sterilized with a short sterilizing time.

The typical conditions for the high temperature and high pressure steam sterilization (autoclave process or autoclave sterilization) are stipulated by American standards ANSI/AAMIST37-1992 approved by American National Standards Institute and issued by Medical Instrument Development Association. According to the conditions, the sterilizing process is carried out at 132° C. for four minutes in a prevacuum type that depressurizes before the sterilizing process and at 132° C. for 10 minutes in a gravity type that does not depressurize before the sterilizing process.

A temperature condition at the sterilizing process of the high pressure steam sterilization differs based on a format of a high pressure steam sterilization device and a time it takes for the sterilizing process. In general, the temperature is set between 115° C. and 138° C. inclusive. The temperature in some of the sterilizing device can be set to substantially 142° C.

A time condition differs based on the temperature condition of the sterilizing process. In general, the time is set between three minutes to sixty minutes inclusive. Some of the different types of the sterilizing device can set the time thereof to 100 minutes. A pressure inside the sterilizing chamber during the process is, in general, set to substantially +0.2 MPa with respect to an atmospheric pressure.

A general high pressure steam sterilizing process of the prevacuum type includes a prevacuuming process that depressurizes inside the sterilizing chamber housing a component to be sterilized before the sterilizing process, and a sterilizing process that performs the sterilization by supplying the high pressure and high temperature steam into the sterilizing chamber after the prevacuuming process.

The prevacuuming process is for infiltrating the steam to every part of the component to be sterilized at the sterilizing process. The high pressure and high temperature steam is supplied to the entire component to be sterilized by depressurizing an interior of the sterilizing chamber. A pressure inside the sterilizing chamber at the prevacuuming process is, in general, set substantially between −0.07 MPa to −0.09 MPa inclusive with respect to the atmospheric pressure.

A drying process might be included in the sterilizing process in order to dry the component to be sterilized after the sterilization. In the drying process, the sterilizing chamber is re-depressurized after the sterilizing process. Specifically, the drying of the component to be sterilized in the sterilizing chamber interior is facilitated by depressurizing the sterilizing chamber interior to remove the steam from the sterilizing chamber interior. A pressure inside the sterilizing chamber at the process is set substantially between −0.07 and −0.09 MPa inclusive with respect to the atmospheric pressure, in general.

Further, an important factor of the exterior member opening 37 is a size thereof. The opening having a size too small cannot follow a speed of a pressure change, and the infiltration of the steam into the endoscope interior 45 is delayed and the sterilizing process inside each of the channels 93, 94, and 95 is delayed. Consequently, the size of the exterior member opening 37 is preferably set to, for example, greater than or equal to 1 mm, and more preferably set to greater than or equal to 5 mm or 10 mm.

Further, an area of the exterior member opening 37, if larger than a clearance area of a portion having the smallest clearance in the endoscope interior 45 that is communicatively connected to the exterior member opening 37, can prevent the exterior member opening 37 from becoming a bottleneck of the steam infiltration.

Further, a filter unit 149, which is an attaching unit formed together with a filter 48 described later, is attached to an exterior periphery of the venting cap 137 having the exterior member opening 37 in such a way that the filter unit 149 covers the exterior periphery of the venting cap 137. When the autoclave process is not performed, a watertight cap 150 described later (see FIG. 4) is attached to the exterior periphery of the venting cap 137 in such a way that the watertight cap 150 covers the filter unit 149.

Figure 3:
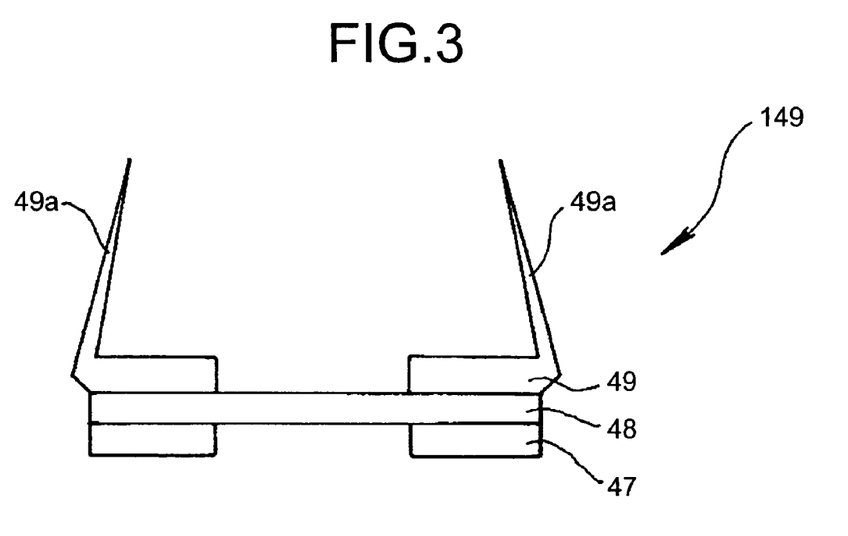
FIG. 3 is a front view of an attaching rubber to which a filter attached to a venting cap disposed at the endoscope in FIG. 2 is disposed.
Figure 4:
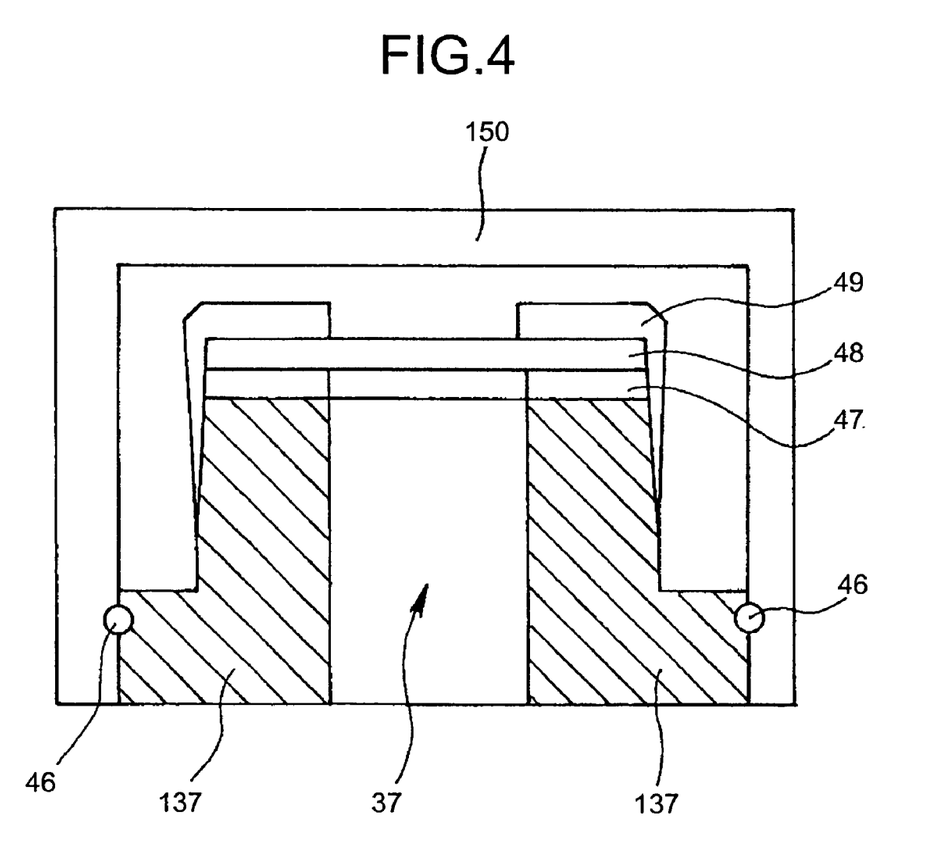
FIG. 4 is an enlarged front view of the venting cap of the endoscope to which the attaching rubber in FIG. 3 and a watertight cap are attached.

For detail, FIG. 3 is a front view of an attaching rubber to which a filter attached to a venting cap disposed at the endoscope in FIG. 2 is disposed, and FIG. 4 is an enlarged front view of the venting cap of the endoscope to which the attaching rubber in FIG. 3 and a watertight cap are attached.

As shown in FIG. 3, the filter unit 149 includes a proximal portion 47 that has a hollow discoidal shape and is made of, for example, a rigid resin, a filter 48 that is disposed on one face of the proximal portion 47, and a discoidal securing portion 49 that is formed from, for example, a silicon rubber. The discoidal securing portion 49 has a fold 49a extended in one direction at an exterior periphery thereof, and is disposed at a face opposite to the face on which the proximal portion 47 of the filter 48 is disposed.

The filter 48 traps a lubricant agent leaking to the outside through the venting cap 137 or dust entering the endoscope interior 45 of the endoscope 2, and preferably traps both of them in order to prevent failure in the endoscope 2. Here, the lubricant agent is applied to, for example, the wire used when the bendable portion 16 (see FIG. 1) of the endoscope 2 is bent.

In order to implement the function described above, the filter 48 is formed from a fine sheet provided with a fine mesh structure that can block, for example, a particle of the lubricant agent and/or the dust. Specifically, the filter 48 is formed from, for example, a sheet member and the like that forms a peel pack that packs the case 34. Here, the case 34 is used to house the endoscope 2 when the sterilizing process is performed.

Further, the filter 48 is preferably formed from a fine sheet serving as a chemical indicator (CI) that changes a color thereof from a first color to a second color when the filter 48 reaches a predetermined temperature. For example, the filter 48 changes the color thereof from white to red when the filter 48 has a temperature of 30° C. or more. Hence, the filter 48 has a function of detecting the temperature of the high temperature and high pressure steam, and the operator can determine whether or not the endoscope 2 has passed the autoclave process just by observing the color of the filter 48.

In order to attach the filter unit 149 configured as described above to the venting cap 137, the operator places the proximal portion 47 of the filter unit 149 on the exterior periphery portion of the distal end of the exterior member opening 37 of the venting cap 137, as shown in FIG. 4. Next, the operator folds back the fold 49a, which extends in one direction, of the securing portion 49. Consequently, the filter unit 149 is attached and secured to the venting cap 137 by tightening of the fold 49a with respect to the exterior periphery side face of the venting cap 137.

Further, when the filter unit 149 is to be detached from the venting cap 137, the fold 49a coming in contact with the exterior periphery face of the securing portion 49 is folded back towards a distal portion direction of the venting cap 137. Consequently, the filter unit 149 is detached from the venting cap 137.

Hence, the filter unit 149 is detachably provided with respect to the venting cap 137.

When the autoclave process is not performed, the watertight cap 150 is attached to the exterior periphery of the venting cap 137 in such a way that the watertight cap 150 covers the filter unit 149. For detail, the watertight cap 150 has a downward depressed shape, and a distal portion thereof is attached to the proximal portion of the exterior periphery side face of the venting cap 137 through an O-ring 46 while keeping airtight state with respect to the venting cap 137.

Hence, the watertight cap 150 is attached with respect to the venting cap 137 independent of the attachment of the filter unit 149 thereto. Therefore, except when the autoclave process is performed, dust do not enter the endoscope interior 45 of the endoscope 2 even if the operator forgets to attach the filter unit 149 to the venting cap 137.

Returning to FIG. 1, the manipulator portion 8 is provided with the air/water supplying manipulator button 28 that manipulates supplying air and water to a second side opposing to the first face, an aspiration manipulator button 29 that manipulates aspiration operation, and the venting cap 138 that has the exterior member opening 38. The venting cap 138 having the exterior member opening 38 is for supplying the high temperature and high pressure steam to the endoscope interior 45 of the endoscope 2 when the autoclave process is performed. In other words, the venting cap 138 is the steam inlet for supplying the steam into the endoscope interior 45.

As similar to the size of the exterior member opening 37, a size of the exterior member opening 38 is, for example, greater than or equal to 1 mm, and preferably greater than or equal to 5 mm or 10 mm. Further, an area of the exterior member opening 38, if larger than the clearance area of the portion having the smallest clearance in the endoscope interior 45 that is communicatively connected to the exterior member opening 38, can prevent the exterior member opening 38 from becoming a bottleneck of the steam infiltration.

Further, the filter unit 149 (see FIG. 4) that is the same as the attaching rubber attached to the venting cap 137 is attached to an exterior periphery of the venting cap 138 having the exterior member opening 38 in such a way that the filter unit 149 covers the exterior periphery of the venting cap 138. Further, the watertight cap 150 (see FIG. 4) that is the same as the watertight cap attached to the exterior periphery of the venting cap 137 is attached to the exterior periphery of the venting cap 138 in such a way that the watertight cap 150 covers the filter unit 149.

Further, the bending manipulator knob 30 for remotely bending the bendable portion 16 is disposed on a third face of the manipulator portion 8.

Pulling effect and relaxant effect is caused on the manipulator wire not shown that is disposed in the endoscope interior 45 of the insertion portion 7 and the manipulator portion 8 by rotating the bending manipulator knob 30. Here, the manipulator wire is connected to a bending mechanism not shown of the bendable portion 16 of the insertion portion 7 and causes a tension and slack of the operation wire not shown. As a result, the bendable portion 16 becomes bendable in four directions of up, down, left, and right; therefore, a visual field direction of the insertion portion 7 can be changed.

Further, a medical instrument insertion opening 32 that is an opening communicatively connected to the medical instrument channel is provided near the insertion portion side bending preventing member 12 of the manipulator portion 8. The medical instrument insertion opening 32 is connected to the aspiration channel 95. Further, a switchbox 55 is provided at an upper end portion of the manipulator portion 8, and a plurality of remote switches 31 that remotely manipulate the video processor 5 are provided on the switchbox 55.

The endoscope 2 configured as described above is housed in the case 34 when the autoclave process is performed, and the case 34 is housed inside the supplying device 60 that performs the autoclave process. The case 34 has a tray 35 that houses the endoscope 2 and a lid member 36 that covers an upper side of the tray 35.

A plurality of venting holes not shown is provided on the tray 35 and on the lid member 36 so that a high temperature and high pressure water vapor supplied into the supplying device 60 can pass through the holes.

The supplying device 60 is a device in which the high temperature and high pressure steam is introduced; however, an explanation thereof is omitted because it is obvious.

As described above, the filter 48 provided in the detachable filter unit 149 serving as the indicator is disposed at the venting cap 137 having the exterior member opening 37 and at the venting cap 138 having the exterior member opening 38, in the endoscope and in the endoscope system according to the first embodiment of the present invention.

The interior of the liquid channel 93, the interior of the air/water channel 94, and the interior of the aspiration channel 95 are heated from outside thereof when each of the channel interiors is sterilized by the autoclave process in which the high temperature and high pressure steam is supplied into the liquid channel 93, the air/water channel 94, and the aspiration channel 95. Consequently, the filter 48 can, for example, trap the lubricant agent applied to the wire used for bending the bendable portion 16 of the endoscope 2 and the dust entering the endoscope interior 45 of the endoscope 2 when the high temperature and high pressure steam enters the endoscope interior 45 from the venting caps 137 and 138 having the exterior member openings 37 and 38 respectively of the endoscope 2. Here, the lubricant agent and the dust flow through the venting caps 137 and 138 by the high temperature and high pressure steam. Hence, the failure of the endoscope 2 due to the lubricant agent leakage and the dust intrusion can be prevented according to the present invention. Therefore, the endurance of the endoscope can be improved.

Further, the filter 48 can be easily changed because the filter 48 is detachable together with the filter unit 149. Furthermore, the operator can determine whether or not the autoclave process is performed on the endoscope 2 just by observing the color of the filter 48 because the filter 48 has the indicator function.

Further, when the operator checks the filter 48 to check the color of the filter 48, the operator can also check a clogging of the filter 48. Thus, the operator cannot forget to change the filter 48.

Further, the watertight cap 150 is provided at the exterior periphery of the venting caps 137 and 138 in such a way that the watertight cap 150 covers the filter unit 149, in the endoscope and the endoscope system according to the first embodiment of the present invention.

Consequently, even if the operator forgets to attach the filter unit 149 to the venting caps 137 and 138, the dust do not enter the endoscope interior 45 of the endoscope 2, except when the autoclave process is performed.

In the present embodiment, the venting caps 137 and 138 are used as an example of the steam inlet of the endoscope interior 45; however, the present invention is not limited to the embodiment. Hence, the number of venting caps can be one or more.

Figure 5:
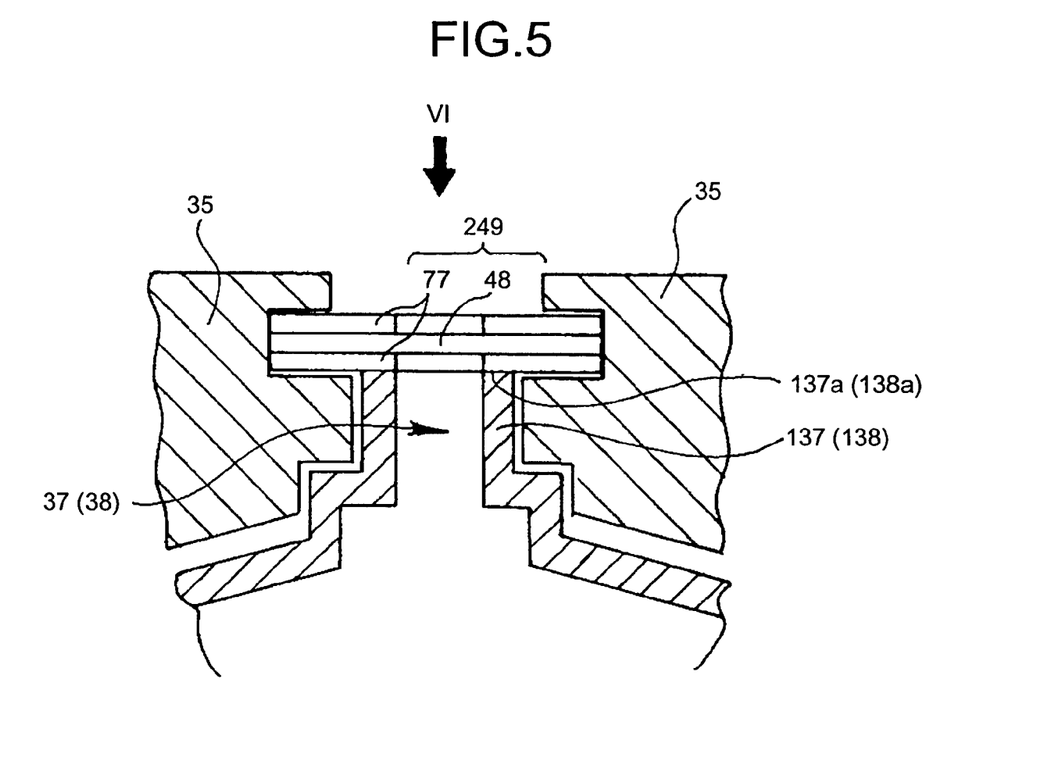
FIG. 5 is an enlarged sectional view showing a steam inlet and a part of a case of the endoscope of the endoscope system according to a second embodiment of the present invention.
Figure 6:
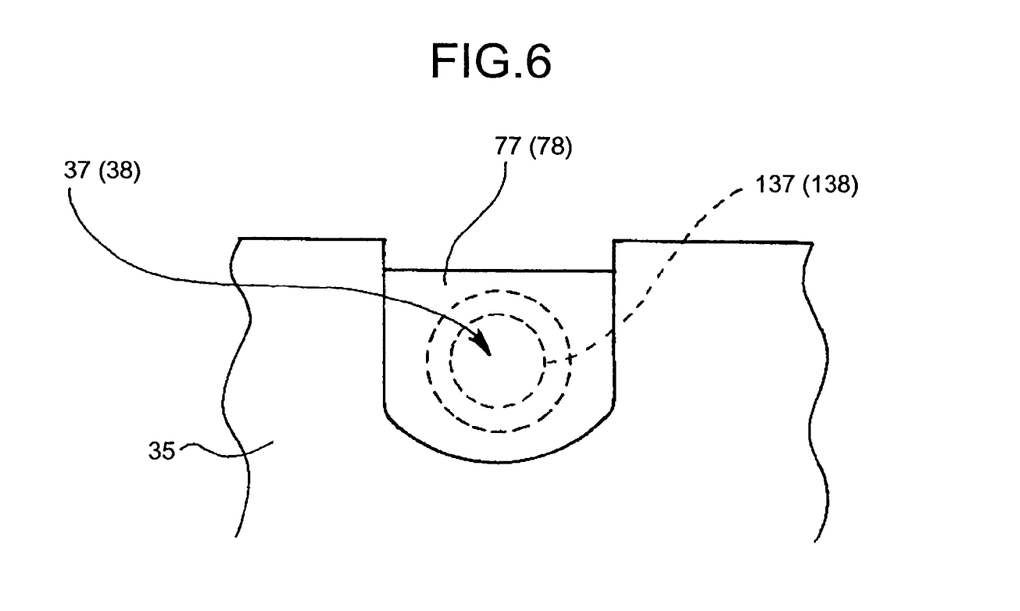
FIG. 6 is a front view of the steam inlet viewed from VI direction of FIG. 5.

FIG. 5 is an enlarged sectional view showing a part of a steam inlet and a case of an endoscope of an endoscope system according to a second embodiment of the present invention, and FIG. 6 is a front view of the steam inlet viewed from VI direction of FIG. 5.

A configuration of the endoscope and the endoscope system according to the second embodiment is substantially the same as that of the endoscope and the endoscope system shown in FIGS. 1 and 2; the difference is only that the filter attached to the steam inlet is disposed in the case in the present embodiment. Hence, only the difference described above will be explained below, and the same numbers are assigned to the same elements as those of the first embodiment, and the explanations thereof will not be repeated. Further, the venting cap 137 is used as an example of the steam inlet for supplying the high temperature and high pressure steam into the endoscope interior 45 of the endoscope 2, in the following explanations.

As shown in FIGS. 5 and 6, a detachable filter unit 249 that is an attaching unit is disposed at a position coming in contact with the exterior member opening 37 of a distal portion 137a of the venting cap 137 when the endoscope 2 is housed in the tray 35 of the case 34.

The filter unit 249 includes the filter 48 and packing members 77 consisting of two hollow disks holding the filter 48 therebetween and formed from, for example, a silicon rubber. Further, the filter 48 and the packing members 77 are formed integrally.

When the endoscope 2 is put in the tray 35 to perform the autoclave process, the exterior member opening 37 of the distal portion 137a of the venting cap 137 of the endoscope 2 is pressed against and comes in contact with the packing member 77 of the filter unit 249 disposed in the tray 35.

As described above, in the endoscope and in the endoscope system according to the second embodiment of the present invention, the filter unit 249, which is closely attaches to the exterior member opening 37 of the distal portion 137a of the venting cap 137, is detachably provided in the tray 35 while the endoscope 2 is housed in the tray 35 of the case 34 during the autoclave process.

Hence, the operator does not forget to attach the filter 48 when the autoclave process is performed because the filter 48 is surely attached to the venting cap 137 when the endoscope 2 is housed in the tray 35.

Further, the operator can remember to detach the watertight cap 150 when the autoclave process is performed, because the endoscope cannot be housed in the tray 35 when the watertight cap 150 of the first embodiment remains attached to the venting cap 137 and hits against a portion outside a housing position of the tray 35.

Further, the same effect as in the first embodiment of the present invention described above can be obtained even if the endoscope system is configured as described above in the present embodiment.

In the present embodiment, the venting cap 137 is used as the example of the venting cap to which the filter unit 249 is attached; however, the present invention is not limited to the embodiment. Thus, the same effect can be obtained when the venting cap 138 having the exterior member opening 38 is applied to the filter unit 249 or other steam inlet is applied to the filter unit 249.

Further, the operator detects the clogging of the filter 48 by visually observing the filter 48 in the first and the second embodiments described above; however, it is not limited thereto. Hence, the detection of the clogging of the filter 48 can be performed by using the venting cap and the watertight cap.

Figure 7:
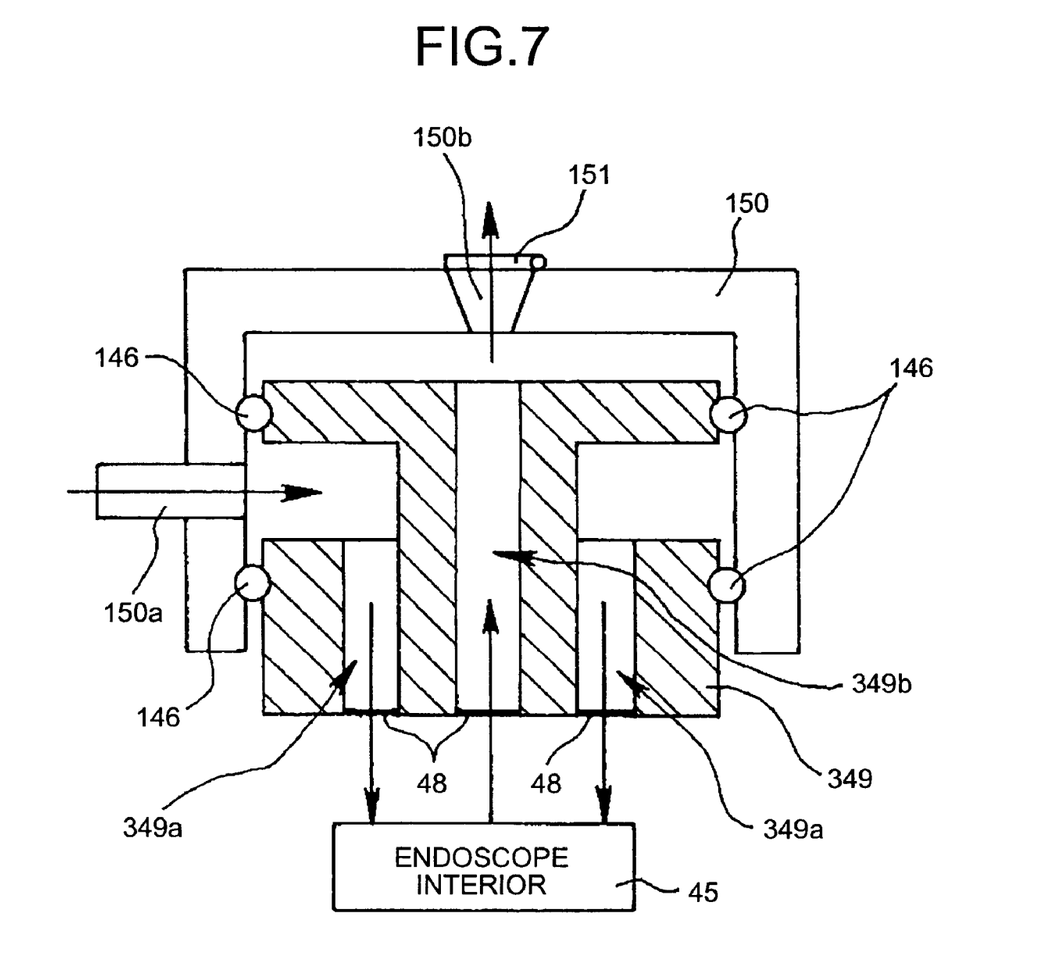
FIG. 7 is a drawing showing another example of a method of a filter clog.

FIG. 7 shows another example of a method for detecting the clogging of the filter to show the above configuration. As shown in FIG. 7, two steam inlets 150a and 150b are formed on the watertight cap 150, and a check valve 151 that is a pressure detecting unit is formed on the steam inlet 150b.

Further, a filter unit 349 is closely attached to and detachably disposed inside the watertight cap 150 through the O-ring 146. The filter unit 349 has basic components including the filter 48 that is disposed at a face coming in contact with the opening of the venting cap of the endoscope, a channel 349a that supplies air from the steam inlet 150a to the venting cap, and a channel 349b that supplies air from the endoscope interior 45 to the steam inlet 150b.

When the detection of the clogging of the filter 48 is performed by using the watertight cap 150 and the filter unit 349 formed as described above, the operator attaches the watertight cap 150 to which the filter unit 349 is disposed to, for example, the venting cap 137.

Next, the operator supplies air from the steam inlet 150a of the watertight cap by using a pressurizing device that is, for example, a pressurizing unit used for a leak test. The supplied air enters the endoscope interior 45 of the endoscope 2 through the channels 349a and the filters 48. Further, the air enters the steam inlet 150b having the check valve 151, through the filters 48 and the channel 349b from the endoscope interior 45.

At the moment, enough mass of air supplied from the steam inlet 150a does not reach the steam inlet 150b if the filter 48 is clogged. In other words, the check valve 151 does not open. Consequently, the operator can determine that the filter 48 is clogged.

Specifically, let P1 be a pressure necessary for the leak test, P2 be a maximum setting pressure of the pressurizing device for the leak test, and P3 be an opening pressure of the check valve 151 necessary for the detection of the clogging, and let the relationship among the P1, P2, and P3 be P1<P2<P3. The operator performs the leak test at the pressure of P1. As a result, if the leak is not caused, the setting pressure of the pressurizing device is set to P3 to confirm the clogging described above.

As described above, different pressures are used to detect even a slight leakage during the leak test. Further, when the air for checking the clogging leaks out from the check valve 151 during the leak test, it is difficult to determine whether the leak is caused at the check valve 151 or at a portion other than the check valve 151. Therefore, the check valve 151 for checking the clogging is closed during the leak test, and the check valve 151 is opened after the leak test at the step for checking the clogging.

Here, when the check valve 151 does not open, in other words, when the filter 48 is clogged, it is equivalent to a state in which permeation efficiency of the filter 48 is, for example, less than or equal to 80% to 85%.

Further, using the watertight cap allows the leak test to be performed in such a way that the operator presses the steam inlet 150b with, for example, his/her finger to supply the air from the steam inlet 150a and thus checks whether or not the air is leaking from other portion of the endoscope 2.

Figure 8:
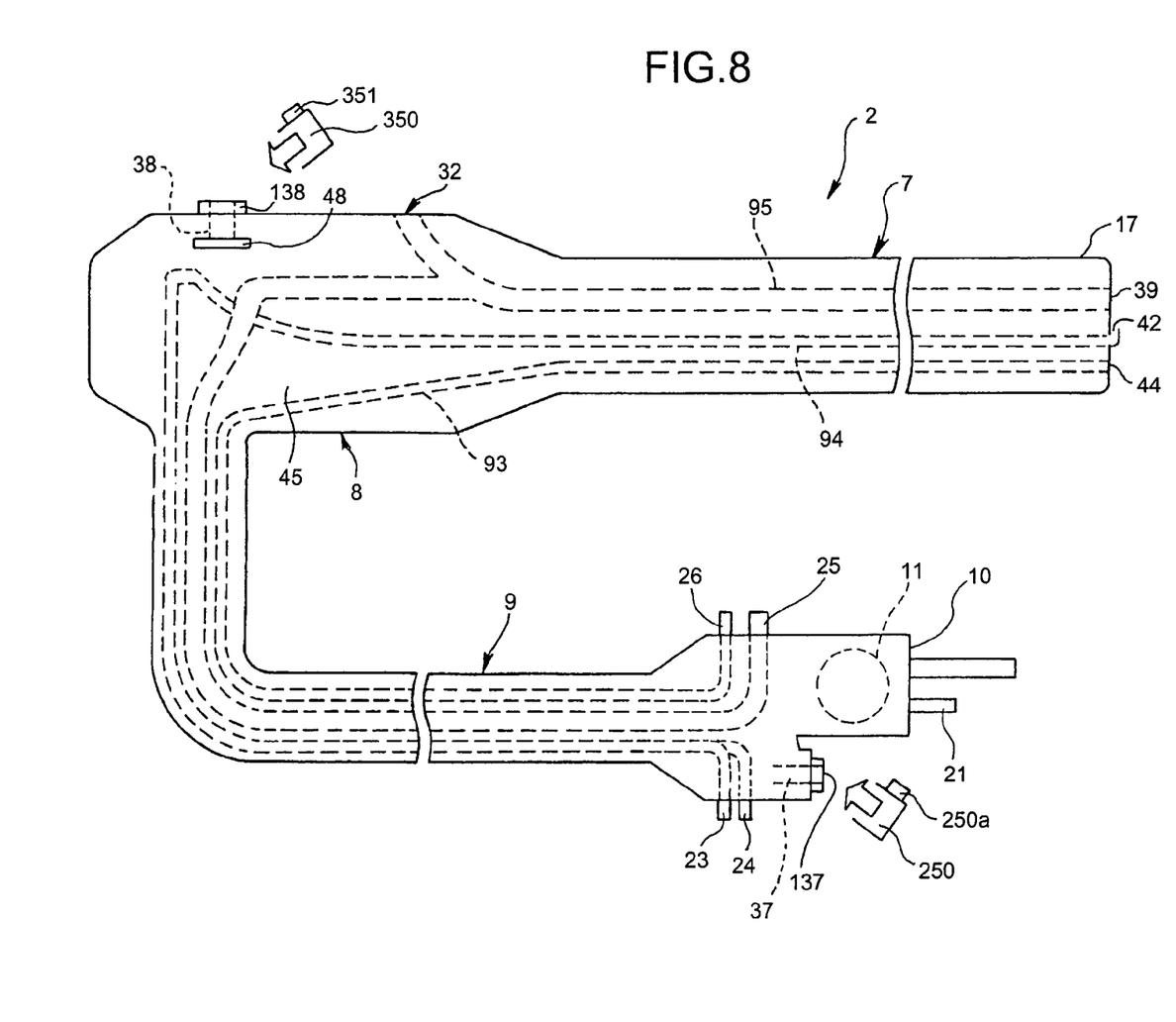
FIG. 8 is a drawing showing still another example of a method of a filter clog.

The detection of the clogging of the filter 48 can be performed by using the venting caps 137, 138, or the electronic connector portion 11. FIG. 8 shows another example of a method for detecting the filter clog. In the following, the method for detecting the filter clog is explained as an example by using the venting caps 137 and 138.

As shown in FIG. 8, the operator attaches a watertight cap 250 having a venting cap 250a for the leak test to the venting cap 137 having the exterior member opening 37. Further, the operator attaches a watertight cap 350 having a check valve 351 to the venting cap 138 having the exterior member opening 38. The watertight caps 250 and 350 are attached to the venting caps 137 and 138 during the time other than performing the autoclave process, as described above.

Next, the operator supplies the air from the venting cap 250a of the watertight cap 250 by using the air supplying device. The supplied air enters the endoscope interior 45 of the endoscope 2, and the air enters the check valve 351 of the watertight cap 350 attached to the venting cap 138 from the endoscope interior 45 through the filter 48.

At this moment, enough amount of the air supplied from the venting cap 250a does not reach the check valve 351 when the filter 48 is clogged. In other words, the check valve 351 does not open. Consequently, the operator can find out that the filter 48 is clogged.

The same effect as described above can be obtained by providing the venting cap at the watertight cap 33 (see FIG. 1) that is to be attached to the electronic connector portion 11 to supply the air from the venting cap.

As described above, the operator can detect the clog of the filter as similar to the leak test.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:

an endoscope including an insertion portion, a channel member that has one opening at a distal portion of the insertion portion and other opening at a portion other than the distal portion, an exterior member opening that communicatively connects an interior of the endoscope to outside and a filter unit that is provided at the exterior member opening to prevent at least one of intrusion of dust into the interior and leakage of a lubricant agent stored in the endoscope out of the endoscope; and a high temperature and high pressure steam supplying unit that supplies high temperature and high pressure steam into the interior of the endoscope from the exterior member opening and into the channel member from the opening; and the filter unit includes a filter, and an attaching unit formed integrally with the filter and attached to an exterior periphery portion of the exterior member opening to cover the exterior periphery portion, the filter being formed from a fine sheet serving as a chemical indicator that changes color thereof from a first color to a second color when the temperature of the filter is greater than or equal to a predetermined temperature.

2. The endoscope system according to claim 1, wherein the high temperature and high pressure steam supplying unit facilitates sterilization of an interior of the channel member by supplying the high temperature and high pressure steam into the interior of the endoscope from the exterior member opening.

3. The endoscope system according to claim 1, further comprising
a watertight cap that is detachably attached to the exterior member opening to cover the attaching unit.

4. The endoscope system according to claim 1, further comprising a housing unit that houses the endoscope when the high temperature and high pressure steam is supplied to the endoscope by the high temperature and high pressure steam supplying unit, wherein the filter is disposed at a position of the housing unit coming in contact with the exterior member opening when the endoscope is housed in the housing unit.

5. The endoscope system according to claim 4, wherein the housing unit has a part coming in contact with the watertight cap at a position other than a housing position of the endoscope.

6. The endoscope system according to claim 5, wherein the watertight cap includes a clog detecting unit that detects clogging of the filter.

7. The endoscope system according to claim 6, wherein the clog detecting unit has at least two steam inlets, at least one of the steam inlets being provided with a pressure detecting unit.

8. The endoscope system according to claim 7, wherein the pressure detecting unit includes a check valve.

9. The endoscope system according to claim 6, wherein the pressure detecting unit detects the clogging of the filter by the check valve that detects a pressure of air coming from the interior of the endoscope through the filter after entering the interior of the endoscope from one of the steam inlets through the filter.

10. The endoscope system according to claim 9, wherein the one of the steam inlets is a communicative connection hole for a leak test that is disposed in the endoscope and is communicatively connected to the steam inlet in which the pressure detecting unit is disposed.

11. The endoscope system according to claim 10, wherein a pressurizing unit used for the leak test supplies the air to the communicative connection hole.

* * * * *